(12) United States Patent
Lu (10) Patent No.: US 10,131,226 B1
(45) Date of Patent: Nov. 20, 2018

(54) HUMAN PERCEPTION TEST SYSTEM AND METHOD THEREOF

(71) Applicant: Primax Electronics Ltd., Taipei (TW)

(72) Inventor: Tsung-Yi Lu, Taipei (TW)

(73) Assignee: PRIMAX ELECTRONICS LTD., Taipei (TW)

( * ) Notice: Subject to any disclaimer, the term of this patent is extended or adjusted under 35 U.S.C. 154(b) by 0 days.

(21) Appl. No.: 15/790,804

(22) Filed: Oct. 23, 2017

(30) Foreign Application Priority Data

May 19, 2017 (TW) .............................. 106116689 A (51) Int. Cl.
*B60K 28/06* (2006.01)
*A61B 5/18* (2006.01)
*A61B 5/16* (2006.01)

(52) U.S. Cl.
CPC .............. *B60K 28/06* (2013.01); *A61B 5/162* (2013.01); *A61B 5/18* (2013.01); *B60W 2540/22* (2013.01)

(58) Field of Classification Search
CPC .......... B60K 285/06; A61B 5/162; A61B 5/18
USPC ........................................................ 340/576
See application file for complete search history.

(56) References Cited

U.S. PATENT DOCUMENTS

| | | | | |
|---|---|---|---|---|
| 6,129,436 A | * | 10/2000 | Treskov | A61B 3/032 351/201 |
| 8,776,173 B2 | * | 7/2014 | Paxton | G06F 21/316 382/120 |
| 2009/0249476 A1 | * | 10/2009 | Seacat | G06F 21/31 726/17 |
| 2012/0054834 A1 | * | 3/2012 | King | G06F 21/31 726/4 |
| 2017/0180348 A1 | * | 6/2017 | Piccolotto | G06K 9/00906 |
| 2017/0316191 A1 | * | 11/2017 | Sipos | G06F 21/31 |

* cited by examiner

*Primary Examiner* — Omar Casillashernandez
(74) *Attorney, Agent, or Firm* — Kirton McConkie; Evan R Witt (57) ABSTRACT

The present invention provides a human perception test system, which performs a human perception test. The human perception test program and presents on the display module a human perception test interface; the human perception test interface is configured to display a graphic box and an arbitrarily moving graphic; a user operates the control unit to control the graphic box, so that the graphic box and the graphic perform synchronous displacement; when the period of time of the synchronous displacement is equal to a preset time value, two moving speeds of the graphic box within the period of time of the synchronous displacement are acquired; and the micro control unit determines, according to an absolute value of a difference between the two moving speeds, whether the user succeeds in the human perception test.

14 Claims, 7 Drawing Sheets

HUMAN PERCEPTION TEST SYSTEM AND METHOD THEREOF

FIELD OF THE INVENTION

The present invention relates to the application field of physical condition tests, and in particular, to a mental state test system and an operating method thereof.

BACKGROUND OF THE INVENTION

Automobiles are quite popular transport tools nowadays. However, with the high popularity rate, there are also frequent traffic accidents caused by drunken driving or fatigue driving, broadcast in social news.

To reduce occurrence of traffic accidents, a plurality of test systems for testing mental states also start to be used in transport tools. For example, Chinese Patent with No. 201631208U discloses an in-vehicle driver reaction sensitivity testing device. Before a vehicle is started, an engine control unit (ECU) turns on an indicator and starts timing, the driver immediately presses a button to stop timing after finding that the indicator is turned on, and duration between turn-on of the indicator and press of the button is used as an index of reaction sensitivity of the driver. A short duration indicates a high sensitivity of the driver. After a plurality of tests, an average of the test results is used as a basis for determining the sensitivity of the driver. Moreover, according to the result of sensitivity determining, a security prompt during driving is provided to the driver or the driver is prohibited from starting the vehicle.

However, although the prior art provides a testing device for testing reaction sensitivity of a driver, the delay tests of the prior art can only measures an instant reaction speed of the driver, and cannot evaluate or learn about data, such as coordination of hands and brain ability, focus ability, and mental state, required for the driver during long time driving. In view of the above, effect of the conventional testing technology on improvement of driving security is limited.

Therefore, how to completely evaluate the coordination of hands and brain ability, focus ability, and mental state of a driver so as to improve security during driving is a technical problem to be resolved by the present invention.

SUMMARY OF THE INVENTION

A main objective of the present invention lies in providing a human perception test system, which performs a human perception test by using an electronic device. The system includes:
  a display module;
  a micro control unit;
  a memory unit, configured to store a human perception test program; and
  a control unit, where
  the micro control unit executes the human perception test program and presents on the display module a human perception test interface; the human perception test interface is configured to display a graphic box and an arbitrarily moving graphic; a user operates the control unit to control the graphic box, so that the graphic box and the graphic perform synchronous displacement; when the period of time of the synchronous displacement is equal to a preset time value, two moving speeds of the graphic box within the period of time of the synchronous displacement are acquired; and the micro control unit determines, according to an absolute value of a difference between the two moving speeds, whether the user succeeds in the human perception test.

In the preferable implementation manner, the electronic device is a remote control device of a transport vehicle.

In the preferable implementation manner, the diameter or coverage of the graphic is capable of being arbitrarily changed.

In the preferable implementation manner, the user operates the control unit to adjust the diameter or coverage of the graphic box.

In the preferable implementation manner, when the period of time of the synchronous displacement is less than the preset time value, the micro control unit determines that the user fails in the human perception test.

In the preferable implementation manner, the micro control unit further generates a warning signal and displays the warning signal on the display module.

In the preferable implementation manner, when the absolute value of the difference between the two moving speeds is equal to or less than a preset speed difference, the micro control unit determines that the user succeeds in the human perception test.

In the preferable implementation manner, the micro control unit further generates a test successful signal and displays the test successful signal on the display module.

In the preferable implementation manner, when the absolute value of the difference between the two moving speeds is greater than a preset speed difference, the micro control unit determines that the user fails in the human perception test.

In the preferable implementation manner, the micro control unit further generates a warning signal and displays the warning signal on the display module.

In the preferable implementation manner, the control unit is a capacitive pressure sensor, a piezoelectric pressure sensor, or a piezoresistive pressure sensor.

The present invention further provides a human perception test method, which performs a human perception test by using an electronic device. The method includes the following steps:
  (a). displaying a graphic and a graphic box on a display module;
  (b). arbitrarily moving the graphic within the display module;
  (c). controlling, by a user, the graphic box to move within the display module by using a control unit;
  (d). determining whether the graphic box encloses the graphic and an outer edge of the graphic does not contact an inner edge of the graphic box; if not, repeatedly performing step (d); or if yes, performing the next step;
  (e). performing synchronous displacement on the graphic box and the graphic, and starting to count a period of time T of the synchronous displacement;
  (f). determining whether the outer edge of the graphic contacts the inner edge of the graphic box during the synchronous displacement; if yes, generating a warning signal; or if not, performing the next step;
  (g). determining whether the period of time T of the synchronous displacement is equal to a preset time value Tset; if not, returning to step (f); or if yes, performing the next step;
  (h). acquiring moving speeds St1 and St2 of the graphic box at two time points within a period of time T of the synchronous displacement;

(i). determining whether an absolute value of (St1-St2) is equal to or less than a preset speed difference PS; if not, generating a warning signal; or if yes, performing the next step; and (j). generating a test successful signal.

In the preferable implementation manner, in step (b), the graphic arbitrarily moves within the display module and the diameter Dc or coverage of the graphic is arbitrarily changed.

In the preferable implementation manner, in step (c), the user controls the graphic box to move within the display module by using the control unit and adjusts the diameter Df or coverage of the graphic box by using the control unit.

DETAILED DESCRIPTION OF THE PREFERRED EMBODIMENT

Advantages, features, and methods for achieving the advantages and features of the present invention are made more comprehensible by describing in detail in the exemplary embodiments with reference to the accompanying drawings. However, the present invention may be implemented in different forms, and should not be limited to the embodiments stated herein. On the contrary, for those of ordinary skill in the art, the embodiments provided herein make the present disclosure more thorough and comprehensive and completely transfer the protection scope of the present invention.

Figure 1:
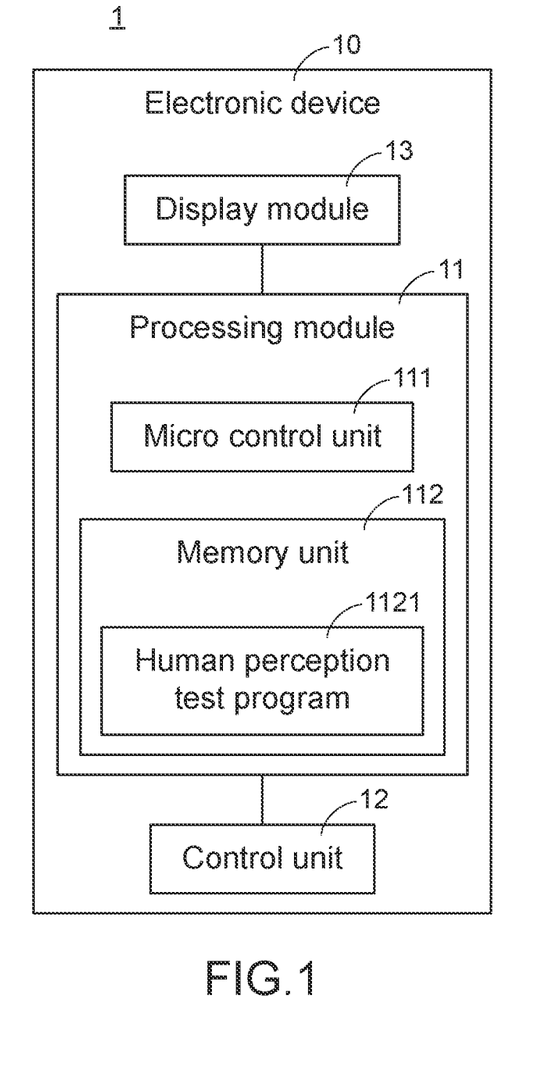
FIG. 1 illustrates a human perception test system of the present invention.

First, referring to FIG. 1, FIG. 1 illustrates a human perception test system of the present invention. In FIG. 1, a human perception test system 1 performs a human perception test by using an electronic device 10. The electronic device 10 in which the human perception test system 1 is installed includes: a processing module 11, a control unit 12, and a display module 13. The processing module 11 is provided with a micro control unit 111 and a memory unit 112. A human perception test program 1121 is stored in the memory unit 112. The micro control unit 111 is a microcontroller or a microprocessor and is configured to execute the human perception test program 1121 in the memory unit 112 and display on the display module 13 a human perception test interface, so that a user may operate the control unit 12 to perform a human perception test on the human perception test interface displayed on the display module 13. The electronic device 10 may be a remote control device of a transport vehicle, and may provide a security prompt to the user or prohibit the user from starting the transport vehicle according to the test result of the human perception test. The transport vehicle may be an automobile, a scooter, an electric vehicle, a rail way train, an aircraft, or a ship.

Figure 2:
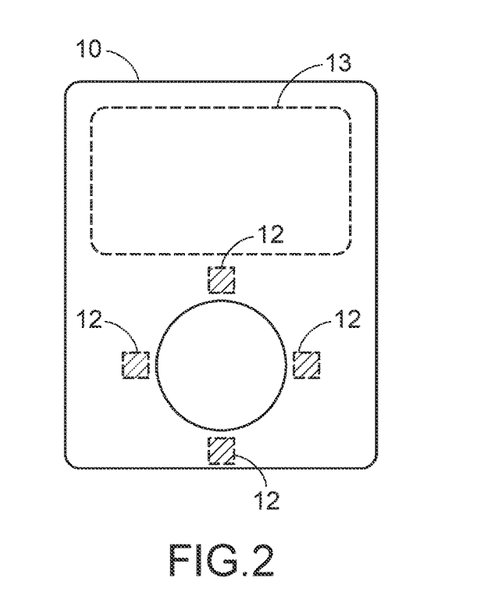
FIG. 2 is a schematic diagram of an electronic device using the human perception test system of the present invention.

Referring to FIG. 2, FIG. 2 is a schematic diagram of an electronic device using the human perception test system of the present invention. The electronic device 10 includes a display module 13 and a plurality of control units 12. The display module 13 may be a liquid-crystal display (LCD) or electronic paper displays (EPD). The control unit 12 is a pressure sensing unit, which may be a capacitive pressure sensor, a piezoelectric pressure sensor, or a piezoresistive pressure sensor. Although the present invention only provides an implementation manner of configuring control units 12 at four directions below the display module 13, in actual application, the configuration form of the control units 12 may be adjusted according to the type of the human perception test program 1121 or the operating mode of the human perception test interface, or one or more control units 12 are configured. The present invention is not limited to the configuration methods provided herein.

Figure 3A:
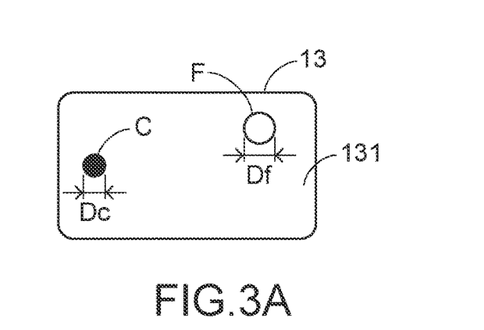
FIG. 3A to FIG. 3F and FIG. 4A to FIG. 4B are schematic diagrams of an electronic device during a human perception test of the present invention.

Subsequently, referring to FIG. 1, FIG. 3A to FIG. 3E and FIG. 4A to FIG. 4B, FIG. 3A to FIG. 3E and FIG. 4A to FIG. 4B are schematic diagrams of an electronic device during a human perception test of the present invention. In FIG. 3A, the micro control unit 111 executes the human perception test program 1121 in the memory unit 112 and displays a human perception test interface 131 on the display module 13. The human perception test interface 131 may display a graphic C that is filled with a color and a graphic box F. In a preferable implementation manner, the graphic C is a bold dot filled with a color, and the graphic box F is a corresponding circular frame line. The graphic C has a diameter Dc, and the diameter Dc or coverage of the graphic C can be arbitrarily changed in a moving process. The graphic box F has a diameter Df. On one hand, a user may control the control unit 12 to control the graphic box F to move on the human perception test interface 131, and may also operate the control unit 12 to adjust the diameter Df or coverage of the graphic box F. For example, when the user gradually increases the force applied onto the control unit 12 by pressing, the diameter Df or coverage of the graphic box F gradually increases. When the user gradually reduces the force applied onto the control unit 12 by pressing, the diameter Df or coverage of the graphic box F gradually reduces. Although the present invention only provides the implementation manner in which the graphic C and graphic box F are circular patterns, in actual application, the graphic C and graphic box F may be in various geometric figures, including: triangles, quadrangles, or polygons. The present invention is not limited to the implementation manners of the graphic patterns. In addition, the present invention may also adjust the level of difficulty of the human perception test by changing the pattern shapes of the graphic C and the graphic box F.

Figure 3B:
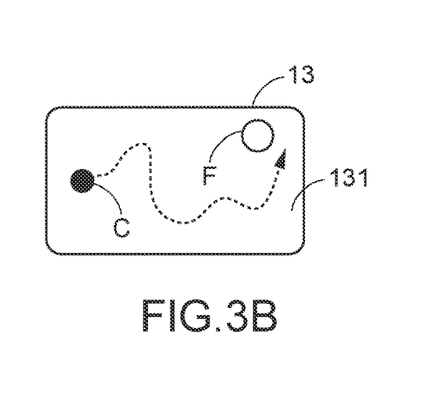
Figure 3C:
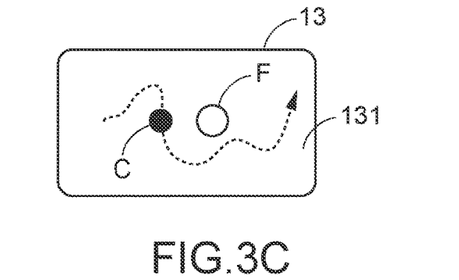
Figure 3D:
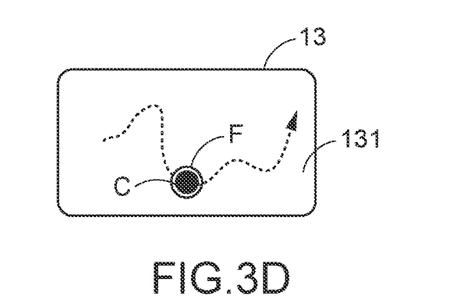
Figure 3E:
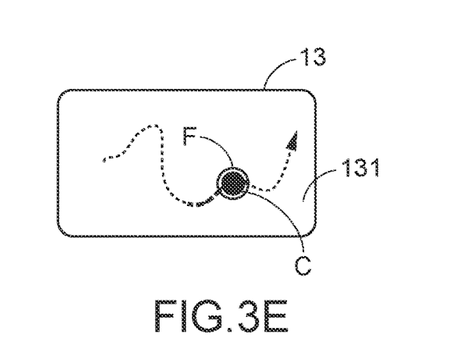
Figure 3F:
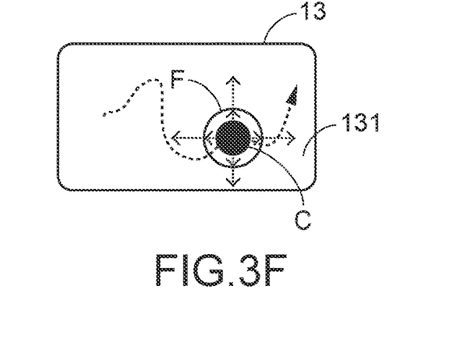

Subsequently, in FIG. 3B, when the human perception test starts, the graphic C arbitrarily and irregularly moves on the human perception test interface 131 displayed on the display module 13, and the diameter Dc or coverage of the graphic C can be arbitrarily changed in the moving process. At this time, the user may operate the control unit 12 to control the moving direction of the graphic box F. In FIG. 3C, the user operates the control unit 12 to control movement of the graphic box F and enable the graphic box F to approach the graphic C. In FIG. 3D, the user operates the control unit 12 to control movement of the graphic box F and enable the graphic box F to enclose the graphic C. At this time, if an outer edge of the graphic C does not contact an inner edge of the graphic box F, the micro control unit 111 determines that the graphic box F and graphic C satisfy an initial condition for synchronous displacement and starts to count a period of time of the synchronous displacement. In FIG. 3E, the user operates the control unit 12 to control the graphic box F, and enable the graphic box F to enclose the graphic C and perform synchronous displacement along with the graphic C. In FIG. 3F, during the synchronous displacement, if the diameter Dc or coverage of the graphic C increases, the user may increase the force applied to the control unit 12 by pressing, so as to enable the diameter Df or coverage of the graphic box F to increase correspondingly, and that the outer edge of the graphic C cannot contact the inner edge of the graphic box F.

Figure 4A:
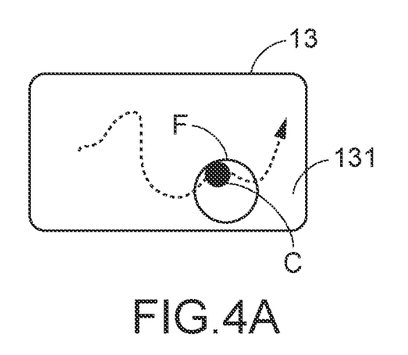
Figure 4B:
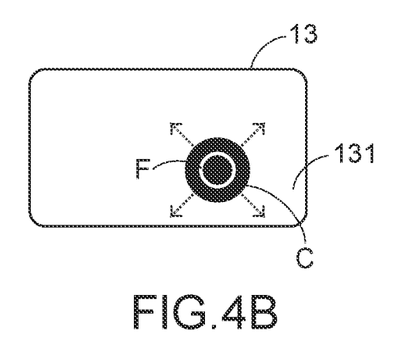

Subsequently, referring to FIG. 4A and FIG. 4B, in FIG. 4A, if the user cannot accurately control movement of the graphic box F by using the control unit 12, which results in that the outer edge of the graphic C contacts the inner edge of the graphic box F, or in FIG. 4B, the user cannot correspondingly operates the control unit 12 to increase the diameter Df or coverage of the graphic box F when the diameter Dc or coverage of the graphic C arbitrarily increases in the moving process, which results in that the outer edge of the graphic C contacts the inner edge of the graphic box F, or even exceeds the coverage of the graphic box F (the reverse display region), the micro control unit 111 determines that the user fails in the human perception test. At this time, the electronic device 10 generates a warning signal and displays the warning signal on the display module 13, for providing security prompt for the user, and informing the user of that the current mental state is not suitable for driving the transport vehicle, or even prohibiting the user from starting the transport vehicle. On the contrary, if the graphic box F operated by the user can perform synchronous displacement along with the graphic C and meanwhile the situation in FIG. 4A or FIG. 4B does not appear, the period of time of the synchronous displacement is equal to a preset time value preset in the human perception test program 1121, and there is not a significant difference in the moving speed of the graphic box F during the synchronous displacement, the micro control unit 111 determines that the user succeeds in the human perception test. At this time, the electronic device 10 generates a test successful signal and displays the test successful signal on the display module 13, thereby informing the user of that the current mental state is suitable for driving the transport vehicle, and further assisting the user to start the transport vehicle.

Figure 5A:
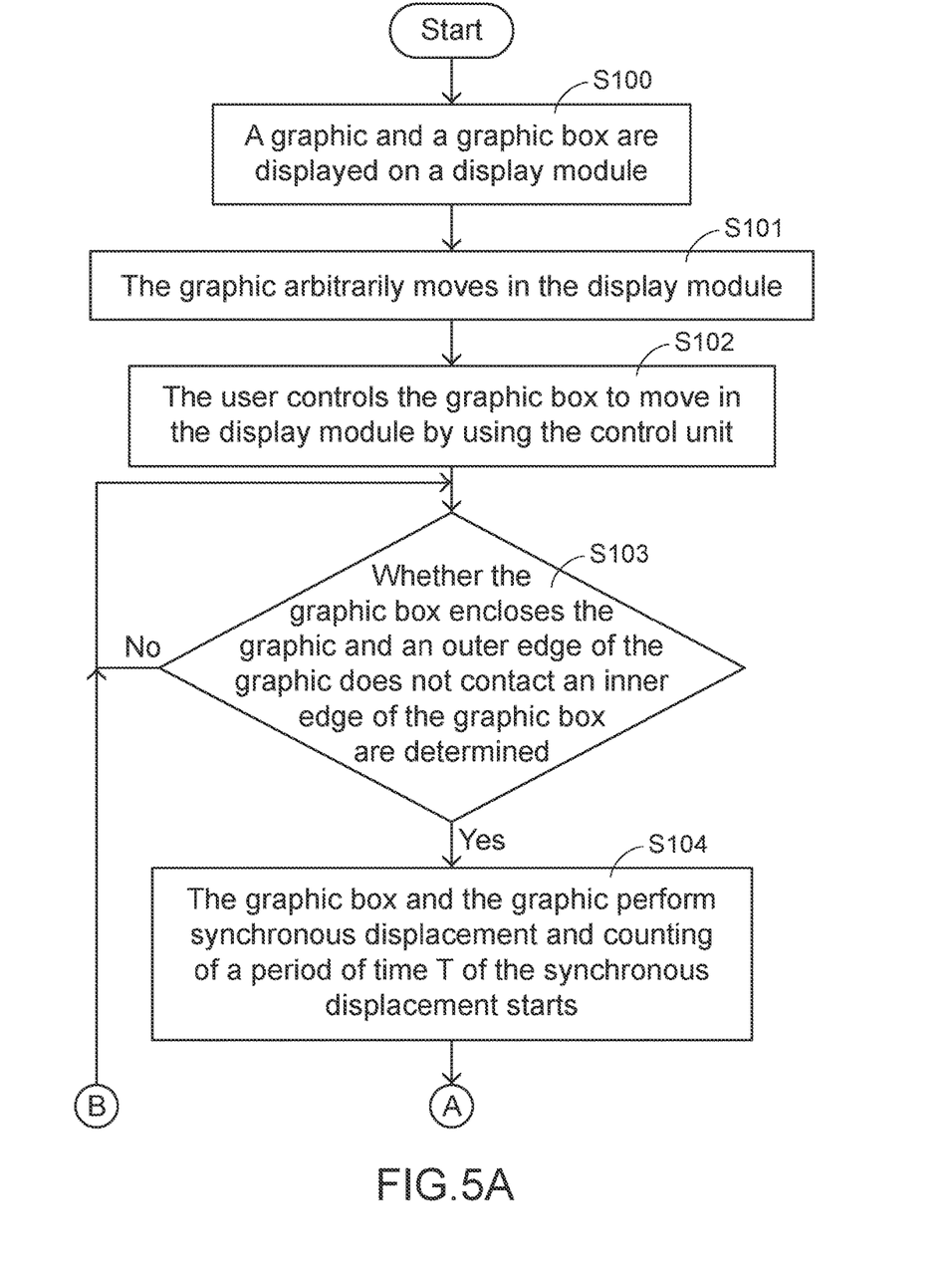
FIG. 5A to FIG. 5B are flowcharts of testing methods of the human perception test system of the present invention.

Referring to FIG. 1, FIG. 3A, and FIG. 5A to FIG. 5B, FIG. 5A to FIG. 5B are flowcharts of testing methods of the human perception test system of the present invention. In FIG. 5A, first a graphic C and a graphic box F are displayed on a display module 13 (step S100). In step S100, the micro control unit 111 executes the human perception test program 1121 in the memory unit 112 and displays a human perception test interface 131 on the display module 13. The human perception test interface 131 may display the graphic box F and the graphic C filled with a color. In a preferable implementation manner, the graphic C has a diameter Dc, and the graphic box F has a diameter Df. Subsequently, the graphic C arbitrarily moves in the display module 13 (step S101), and the user controls the graphic box F to move in the display module 13 by using the control unit 12 (step S102). In the process in which the graphic box F moves in the display module 13, whether the graphic box F encloses the graphic C and an outer edge of the graphic C does not contact an inner edge of the graphic box F are determined (step S103). In step S103, if the determined result is not, step S103 is repeatedly performed; if the determined result is yes, it indicates that the graphic box F and the graphic C satisfy an initial condition for synchronous displacement, and the graphic box F and the graphic C perform synchronous displacement and counting of a period of time T of the synchronous displacement starts (step S104).

Figure 5B:
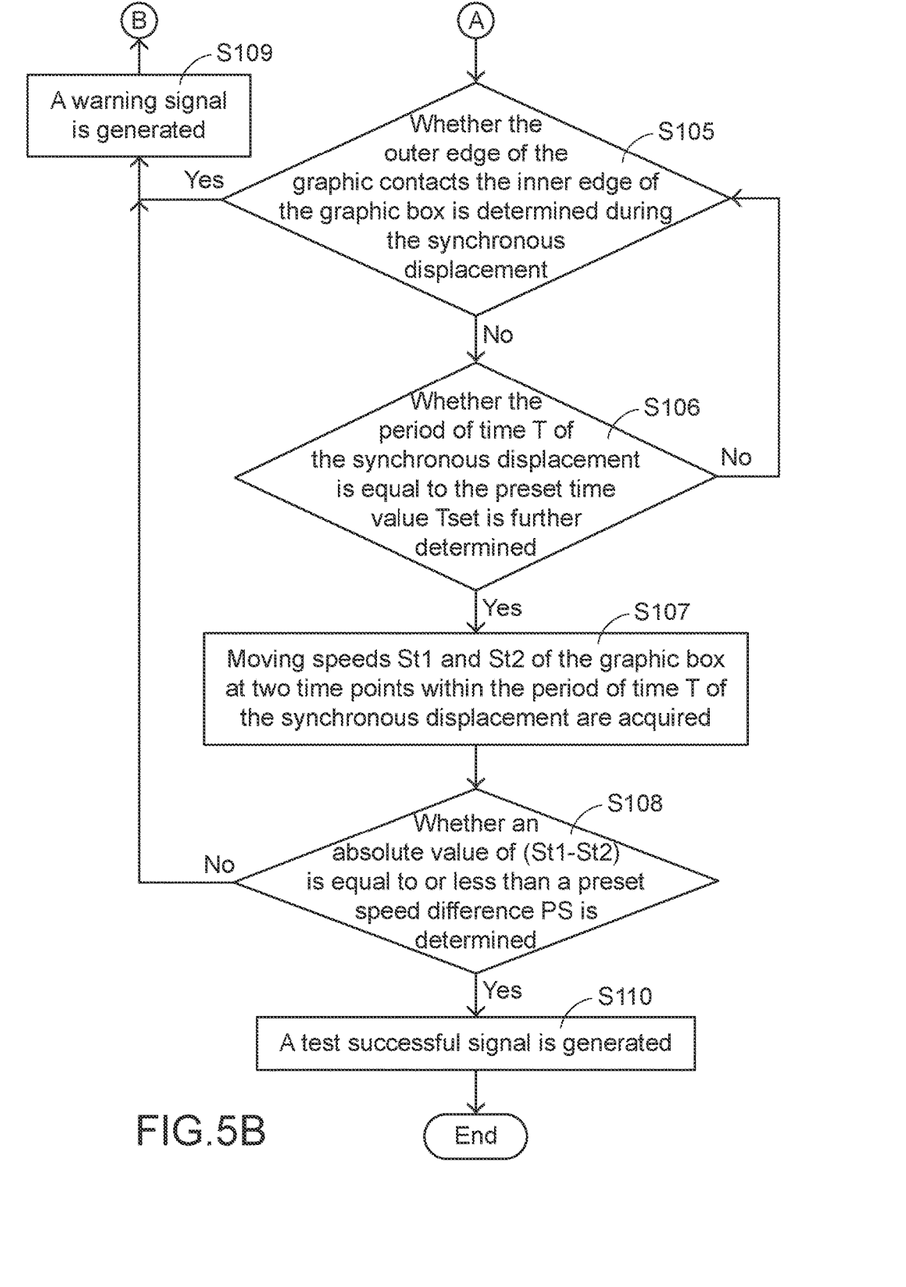

Still referring to FIG. 5B, during the synchronous displacement, whether the outer edge of the graphic C contacts the inner edge of the graphic box F is determined (step S105). In step S105, if the determined result is yes, counting of the period of time T of the synchronous displacement is ended, and a warning signal is generated (step S109). In step S109, the generated warning signal may be displayed on the display module 13, thereby informing the user of that the user fails in the human perception test. The user can learn about that the mental state is not good. In step S105, if the determined result is not, whether the period of time T of the synchronous displacement is equal to the preset time value Tset is further determined (step S106). In step S106, if the preset time value Tset is in a range between 1 s to 10 s, and the determined result is not, step S105 is returned. In step S106, if the determined result is yes, counting of the period of time T of the synchronous displacement is ended, and moving speeds St1 and St2 of the graphic box F at two time points within the period of time T of the synchronous displacement are acquired (step S107). In step S107, two time points t1 and t2 at which moving speed acquisition is to be performed may be set by using the human perception test program 1121. For example, the time points t1 and t2 are set in a primary phase of the synchronous displacement, and the moving speeds St1 and St2 of the graphic box F are acquired in the primary phase of the synchronous displacement, or the time points t1 and t2 are set in an intermediate phase of the synchronous displacement, and the moving speeds St1 and St2 of the graphic box F are acquired in the intermediate phase of the synchronous displacement, or the time points t1 and t2 are set in a post phase of the synchronous displacement, and the moving speeds St1 and St2 of the graphic box F are acquired in the post phase of the synchronous displacement. In addition, the time points t1 and t2 may also be set in any two of the primary phase, the intermediate phase, and the post phase of the synchronous displacement. For example, the time point t1 may be set in the primary phase of the synchronous displacement and the moving speed St1 of the graphic box F is acquired in the primary phase of the synchronous displacement, and the time point t2 is set in the intermediate phase of the synchronous displacement and the moving speed St2 of the graphic box F is acquired in the intermediate phase of the synchronous displacement. For example, if the period of time T of the synchronous displacement is equal to 9 s, the time point t1 is set in a range of 0 s to 3 s and the moving speed St1 of the graphic box F is acquired in the range of 0 s to 3 s, and the time point t2 is set in a range of 3 s to 6 s and the moving speed St2 of the graphic box F is acquired in the range of 3 s to 6 s.

Subsequently, whether an absolute value of (St1-St2) is equal to or less than a preset speed difference PS is determined (step S108). In step S108, the absolute value of (St1-St2) is used for evaluating the focus ability and mental state of the user, for determining whether the user can control the graphic box F to move at a stable speed. The preset speed difference PS may be a real number in a range of 0 to 1. If the determined result in step S108 is not, step S109 is returned; or if the determined result in step S108 is yes, a test successful signal is generated (step S110). In step S110, the generated test successful signal may be displayed on the display module 13, thereby informing the user of that the user succeeds in the human perception test. The user may learn about that the focus ability is good and the mental state is stable.

Figure 5C:
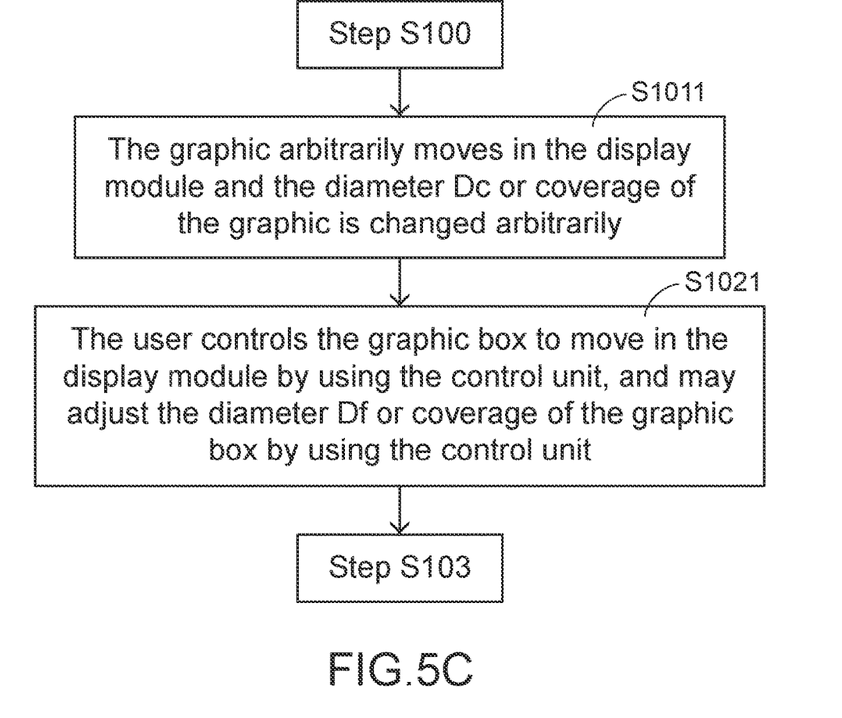
FIG. 5C is a detailed exploded flowchart of step S101 and step S102 in FIG. 5A.

Referring to FIG. 5C, FIG. 5C is a detailed exploded flowchart of step S101 and step S102 in FIG. 5A. In FIG. 5C, step S101 further includes the following steps: the graphic C arbitrarily moves in the display module 13 and the diameter Dc or coverage of the graphic C is changed arbitrarily (step S1011). Subsequently, the user controls the graphic box F to move in the display module 13 by using the control unit 12, and may adjust the diameter Df or coverage of the graphic box F by using the control unit 12 (step S1021). In step S1021, the user operates the control unit 12 to adjust the diameter Df or coverage of the graphic box F, to adapt to the change of the diameter Dc or coverage of the graphic C, so as to evaluate the coordination of hands and brain ability of the user. For example, when the diameter Dc or coverage of the graphic C increases, the user correspondingly increases the force applied to the control unit 12 by pressing, to increase the diameter Df or coverage of the graphic box F; when the diameter Dc or coverage of the graphic C reduces, the user may correspondingly reduce the force applied to the control unit 12 by pressing, to reduce the diameter Df or coverage of the graphic box E In conclusion, as compared with the prior art, the human perception test system of the present invention can completely evaluate the coordination of hands and brain ability, focus ability, and mental state of a user before the user drives a vehicle, and can use an electronic device to provide a security prompt to the user, or prohibit the user form starting the transport vehicle, thereby effectively improving security during driving of the transport vehicle. Therefore, the present invention is actually a creation having an industrial value.

Any equivalent changes or modifications made by those of ordinary skill in the art by using any technical measures shall fall within the claims of the present invention.

What is claimed is:

1. A human perception test system, which performs a human perception test by using an electronic device, wherein the system comprises:
    a display module;
    a micro control unit;
    a memory unit, configured to store a human perception test program; and
    a control unit, wherein
    the micro control unit executes the human perception test program and presents on the display module a human perception test interface; the human perception test interface is configured to display a graphic box and an arbitrarily moving graphic; a user operates the control unit to control the graphic box, so that the graphic box and the graphic perform synchronous displacement; when the period of time of the synchronous displacement is equal to a preset time value, two moving speeds of the graphic box within the period of time of the synchronous displacement are acquired; and the micro control unit determines, according to an absolute value of a difference between the two moving speeds, whether the user succeeds in the human perception test.

2. The human perception test system according to claim 1, wherein the electronic device is a remote control device of a transport vehicle.

3. The human perception test system according to claim 1, wherein the diameter or coverage of the graphic is capable of being arbitrarily changed.

4. The human perception test system according to claim 1, wherein the user operates the control unit to adjust the diameter or coverage of the graphic box.

5. The human perception test system according to claim 1, wherein when the period of time of the synchronous displacement is less than the preset time value, the micro control unit determines that the user fails in the human perception test.

6. The human perception test system according to claim 5, wherein the micro control unit further generates a warning signal and displays the warning signal on the display module.

7. The human perception test system according to claim 1, wherein when the absolute value of the difference between the two moving speeds is equal to or less than a preset speed difference, the micro control unit determines that the user succeeds in the human perception test.

8. The human perception test system according to claim 7, wherein the micro control unit further generates a test successful signal and displays the test successful signal on the display module.

9. The human perception test system according to claim 1, wherein when the absolute value of the difference between the two moving speeds is greater than a preset speed difference, the micro control unit determines that the user fails in the human perception test.

10. The human perception test system according to claim 9, wherein the micro control unit further generates a warning signal and displays the warning signal on the display module.

11. The human perception test system according to claim 1, wherein the control unit is a capacitive pressure sensor, a piezoelectric pressure sensor, or a piezoresistive pressure sensor.

12. A human perception test method, which performs a human perception test by using an electronic device, wherein the method comprises the following steps:
    (a) displaying a graphic and a graphic box on a display module;
    (b) arbitrarily moving the graphic within the display module;
    (c) controlling, by a user, the graphic box to move within the display module by using a control unit;
    (d) determining whether the graphic box encloses the graphic and an outer edge of the graphic does not contact an inner edge of the graphic box; if not, repeatedly performing step (d); or if yes, performing the next step;
    (e) performing synchronous displacement on the graphic box and the graphic, and starting to count a period of time T of the synchronous displacement;
    (f) determining whether the outer edge of the graphic contacts the inner edge of the graphic box during the synchronous displacement; if yes, generating a warning signal; or if not, performing the next step;
    (g) determining whether the period of time T of the synchronous displacement is equal to a preset time value Tset; if not, returning to step (f); or if yes, performing the next step;
    (h) acquiring moving speeds St1 and St2 of the graphic box at two time points within a period of time T of the synchronous displacement;
    (i) determining whether an absolute value of (St1-St2) is equal to or less than a preset speed difference PS; if not, generating a warning signal; or if yes, performing the next step; and
    (j) generating a test successful signal.

13. The human perception test method according to claim 12, wherein in step (b), the graphic arbitrarily moves within the display module and the diameter Dc or coverage of the graphic is arbitrarily changed.

14. The human perception test method according to claim 12, wherein in step (c), the user controls the graphic box to move within the display module by using the control unit and adjusts the diameter Df or coverage of the graphic box by using the control unit.

* * * * *